(12) United States Patent
Zhu et al.

(10) Patent No.: US 8,825,169 B2
(45) Date of Patent: Sep. 2, 2014

(54) METHOD FOR ESTIMATING DESIRED STIMULATION AMPLITUDE FOR ELECTRODE CONFIGURATION

(71) Applicant: Boston Scientific Neuromodulation Corporation, Valencia, CA (US)

(72) Inventors: Changfang Zhu, Valencia, CA (US); Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/082,958

(22) Filed: Nov. 18, 2013

(65) Prior Publication Data

US 2014/0081350 A1    Mar. 20, 2014

Related U.S. Application Data

(63) Continuation of application No. 13/335,924, filed on Dec. 22, 2011, now Pat. No. 8,644,947.

(60) Provisional application No. 61/427,027, filed on Dec. 23, 2010.

(51) Int. Cl.
*A61N 1/00*        (2006.01)
(52) U.S. Cl.
USPC .......................................................... 607/59
(58) Field of Classification Search
USPC .......................................................... 607/59
See application file for complete search history.

(56) References Cited

U.S. PATENT DOCUMENTS

| | | | |
|---|---|---|---|
| 6,393,325 B1 | 5/2002 | Mann et al. | |
| 6,487,451 B1 | 11/2002 | Casset et al. | |
| 6,516,227 B1 | 2/2003 | Meadows et al. | |
| 6,731,986 B2 | 5/2004 | Mann | |
| 6,895,280 B2 | 5/2005 | Meadows et al. | |
| 6,993,384 B2 | 1/2006 | Bradley et al. | |
| 7,627,384 B2 | 12/2009 | Ayal et al. | |
| 2007/0203541 A1* | 8/2007 | Goetz et al. ..................... 607/59 |
| 2007/0288064 A1 | 12/2007 | Butson et al. | |
| 2008/0114233 A1 | 5/2008 | McIntyre et al. | |
| 2010/0010566 A1 | 1/2010 | Thacker et al. | |

(Continued)

OTHER PUBLICATIONS

U.S. Appl. No. 61/257,753, System and Method for Mapping Arbitrary Electric Fields to Pre-Existing Lead Electrodes, Inventor: Michael Moffit, filed, Nov. 3, 2009.

(Continued)

*Primary Examiner* — Robert N Wieland
(74) *Attorney, Agent, or Firm* — Vista IP Law Group LLP

(57) ABSTRACT

A method of providing therapy to a patient comprises (a) receiving input from a user, (b) selecting a first electrode configuration in response to receiving the user input, (c) predicting a neural response induced by electrical energy theoretically conveyed by the first electrode configuration at a specified amplitude, (d) deriving a metric value from the predicted neural response, (e) comparing the metric value to a reference threshold value, (f) adjusting the specified amplitude of the electrical energy if the metric value is not in a specified range relative to the reference threshold value, (g) repeating steps (c)-(f) using the adjusted amplitude as the specified amplitude until the metric value is in the specific range relative to the reference threshold value, and (h) instructing a neurostimulation device to deliver the electrical energy at the adjusted amplitude via the first electrode configuration to stimulate the patient.

26 Claims, 9 Drawing Sheets

(56) References Cited

U.S. PATENT DOCUMENTS

2010/0121409 A1 5/2010 Kothandaraman et al.
2011/0093044 A1 4/2011 Moffitt
2011/0106215 A1 5/2011 Moffitt
2012/0046715 A1 2/2012 Moffitt et al.
2012/0165900 A1 6/2012 Zhu et al.

OTHER PUBLICATIONS

U.S. Appl. No. 61/374,879, User Interface for Segmented Neurostimulation Leads, Inventor: Michael A. Moffitt, et al., filed, Aug. 18, 2010.

U.S. Appl. No. 61/427,059, Neurostimulation System for Implementing Model-Based Estimate of Neurostimulation Effects, Inventor: Changfang Zhu, et al., filed, Dec. 23, 2010.

Chaturvedi, A. et al., Patient-specific models of deep brain stimulation: Influence of field model complexity on neural activation predictions, Brain Stimulation (2010) 3, 65-77.

Frankemolle, A.M. et al., Reversing cognitive-motor impairments in Parkinson's disease patients using a computational modelling approach to deep brain stimulation programming, Brain (2010): 133:3, 746-761.

PCT International Search Report for PCT/US2011/067070, Applicant: Boston Scientific Neuromodulation Corporation, Form PCT/ISA/210 and 220, dated Jun. 1, 2012 (5pages).

PCT Written Opinion of the International Search Authority for PCT/US2011/067070, Applicant: Boston Scientific Neuromodulation Corporation, Form PCT/ISA1237, dated Jun. 1, 2012 (5 pages).

Warman, E.N. et al., Modeling the Effects of Electric Fields on Nerve Fibers: Determination of Excitation Thresholds, IEEE Transaction on Biomedical Engineering, vol. 39, No. 12, pp. 1244-1254, Dec. 1992.

\* cited by examiner

METHOD FOR ESTIMATING DESIRED STIMULATION AMPLITUDE FOR ELECTRODE CONFIGURATION

RELATED APPLICATION DATA

The present application is a continuation of U.S. patent Ser. No. 13/335,924, filed Dec. 22, 2011, which claims the benefit under 35 U.S.C. §119 to U.S. provisional patent application Ser. No. 61/427,027, filed Dec. 23, 2010. The foregoing applications are hereby incorporated by reference into the present application in their entirety.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the stimulation region can often be moved back to the effective pain site without having to re-operate on the patient in order to reposition the lead and its electrode array. When adjusting the stimulation region relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. The Bionic Navigator® may use one of two ways to electrically steer the current along the implanted leads.

In one method, described in U.S. Pat. No. 6,393,325, entitled "Directional Programming for Implantable Electrode Arrays", current steering is performed in accordance with a steering or navigation table, which includes a series of reference electrode combinations (for a lead of 8 electrodes) with associated fractionalized current values (i.e., fractionalized electrode configurations). The rows of the navigation table can then be stepped through to gradually steer electrical current from one basic electrode combination to the next, thereby electronically steering the stimulation region along the leads.

In another novel method, described in U.S. Provisional Application Ser. No. 61/257,753, entitled "System and Method for Mapping Arbitrary Electric Fields to Pre-existing Lead Electrodes," which is incorporated herein by reference, a stimulation target in the form of an ideal bipole or tripole is defined and the stimulation parameters, including the fractionalized current values on each of the electrodes, is computationally determined in a manner that emulates these ideal poles. It can be appreciated that current steering can be implemented by moving the ideal bipole or tripole about the leads, such that the appropriate fractionalized current values for the electrodes are computed for each of the various positions of the ideal bipole or tripole.

Because the optimum stimulation energy amplitude required to produce a desired patient outcome depends on the electrode combination used to deliver the stimulation energy, it is desirable to adjust the amplitude of the stimulation energy as the electrode configuration changes (either as a result of operating the computerized programming system in a manual mode or an automated mode), so that stimulation of the targeted tissue can be maintained without causing adverse effects due to over-stimulation, or loss of sensation due to under-stimulation, thereby allowing the optimum electrode configuration or configurations to be identified as efficiently and quickly as possible.

However, the physician or clinician, oftentimes, must manually adjust the amplitude of the stimulation energy several times when transitioning between electrode combinations in order to maintain optimum stimulation of the targeted tissue. This manual adjustment of the stimulation energy amplitude is time consuming and imposes high requirements on the physician's or clinician's knowledge. If a navigation table is utilized, the desired stimulation energy amplitude can be empirically determined for several electrode configurations and incorporated into the navigation table. This empirical method, however, is only applicable to a certain number of known electrode configurations that are typically confined to one neurostimulation lead, since the relative positions between multiple neurostimulation leads will typically vary for each patient. Furthermore, in the case where electrode configurations are selected to emulate an ideal bipole or tripole that is steered relative to the neurostimulation lead(s), there are thousands, if not millions, of different electrode configurations that can be used, and therefore, an empirical method cannot be reasonably used to determine the stimulation amplitudes for the many electrode configurations.

There, thus, remains a need for an improved manner in which to manage the stimulation amplitude during the transition between different electrode configurations.

SUMMARY OF THE INVENTION

In accordance with the present inventions, a neurostimulation system for use in providing therapy to a patient is provided. The neurostimulation system comprises a user input device (e.g., a directional programming device) configured for receiving input from a user, and processing circuitry configured for (a) selecting a first electrode configuration (e.g., a fractionalized electrode configuration) in response to receiving the input from the user via the user input device, and (b) predicting a neural response in the patient induced by electrical energy theoretically conveyed by the first electrode configuration at a specified amplitude (e.g., an amperage value or a voltage value).

In one embodiment, the processing circuitry is configured for predicting the neural response in the patient by estimating a spatial distribution of electrical parameter values (e.g., field potential values, electrical field values, or current density values) induced by electrical energy theoretically conveyed by the first electrode configuration at a unit amplitude value. For example, the processing circuitry may generate an electric field model of the first electrode configuration (e.g., an analytical model or a numerical model), and determine the electrical parameter values based on the electrical field model. The electrical parameter values may be in a linear relationship with the specified amplitude of the electrical energy theoretically conveyed by the first electrode configuration. The processing circuitry may further multiply the electrical parameters by the specified amplitude to obtain a spatial distribution of scaled electrical parameter values. The processing circuitry may further comprise estimating a transmembrane potential of at least one neuronal element in the patient in response to the scaled electrical parameters. For example, the processing circuitry may generate an electrical model of the neuronal element(s) (e.g., a passive neuron model, an active neuron model, or an analog chip based circuit model), and estimate the transmembrane potential based on the electrical model of the neuronal element(s), e.g., using one of an activating function or a total driving function.

The processing circuitry is further configured for (c) deriving a metric value from the predicted neural response, and (d) comparing the metric value to a reference threshold value. In one embodiment, the metric value may be an estimated transmembrane potential of at least one neuronal element, and the reference threshold value may be a threshold transmembrane potential. In another embodiment, the metric value may be an estimated volume of activation, and the reference threshold value may be a threshold volume of activation. In an optional embodiment, the processing circuitry is configured for instructing the neurostimulation device to deliver reference electrical energy at a known amplitude to a reference electrode configuration, adjusting the reference amplitude of the reference electrical energy until a perception threshold of the patient is met or exceeded, estimating a transmembrane potential of at least one reference neuron of the patient that would be induced by the reference electrical energy of the reference amplitude by the reference electrode configuration, and deriving the reference threshold value based on the estimated transmembrane potential of the at least one reference neuron.

The processing circuitry is further configured for (e) adjusting the specified amplitude of the electrical energy if the metric value is not in a specified range relative to the reference threshold value. In one embodiment, the specified amplitude of the electrical energy theoretically conveyed by the first electrode configuration is increased if the metric value is below the reference threshold value, and decreased if the metric value exceeds the reference threshold value by more than a specific difference value.

The processing circuitry is further configured for (f) repeating steps (b)-(e) using the adjusted amplitude (e.g., using uniform increments) as the specified amplitude until the metric value is in the specific range relative to the reference threshold value, and (g) instructing a neurostimulation device to deliver the electrical energy at the adjusted amplitude via the first electrode configuration to stimulate the patient. The processing circuitry may be further configured for selecting a second different electrode configuration in response to receiving the input from the user, and repeating steps (b)-(g) for the second electrode configuration.

In an optional embodiment, the processing circuitry is configured for (h) determining a first scaling factor for the first electrode configuration, (i) instructing the neurostimulation device to deliver the electrical energy at a known amplitude via the first electrode configuration (which may be the adjusted amplitude or a different amplitude) to stimulate the patient; (j) selecting another different electrode configuration in response to receiving the input from the user, (k) repeating steps (b)-(f) for the second electrode configuration, (l) determining a second scaling factor for the second electrode configuration. In one embodiment, the first scaling factor is between the adjusted amplitude for the first electrode configuration and a reference amplitude (e.g., a unit amplitude), and the second scaling factor is between the adjusted amplitude for the second electrode configuration and the reference amplitude. In another embodiment, the first scaling factor is between the metric value for the first electrode configuration and a reference metric value at a reference amplitude, and the second scaling factor is between the metric value for the second electrode configuration and a reference metric value at the reference amplitude.

The processing circuitry in the optional embodiment further comprises (m) computing a boosting factor based on the first and second scaling factors, (n) applying the boosting factor to the known amplitude to generate an estimated amplitude, and (o) instructing the neurostimulation device to deliver the electrical energy at the estimated amplitude via the second electrode configuration to stimulate the patient. In one embodiment, the boosting factor is computed in accordance with the equation $BF=(SF_B-SF_A)/SF_A$, wherein BF is the boosting factor, $SF_A$ is the first scaling factor, and $SF_B$ is the second scaling factor, and the boosting factor is applied to the known amplitude in accordance with the equation $A_{EST}=A_{KNOWN}\times(1+BV)$, where $A_{EST}$ is the estimated amplitude, and $A_{KNOWN}$ is the known amplitude.

In one embodiment, the neurostimulation system further comprises output circuitry configured via which the processing circuitry instructs the neurostimulation device to actually deliver the electrical energy at the adjustable amplitude to the first electrode configuration. The neurostimulation system may further comprise a housing containing the user interface device and the processing circuitry, all of which may be included in an external control device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
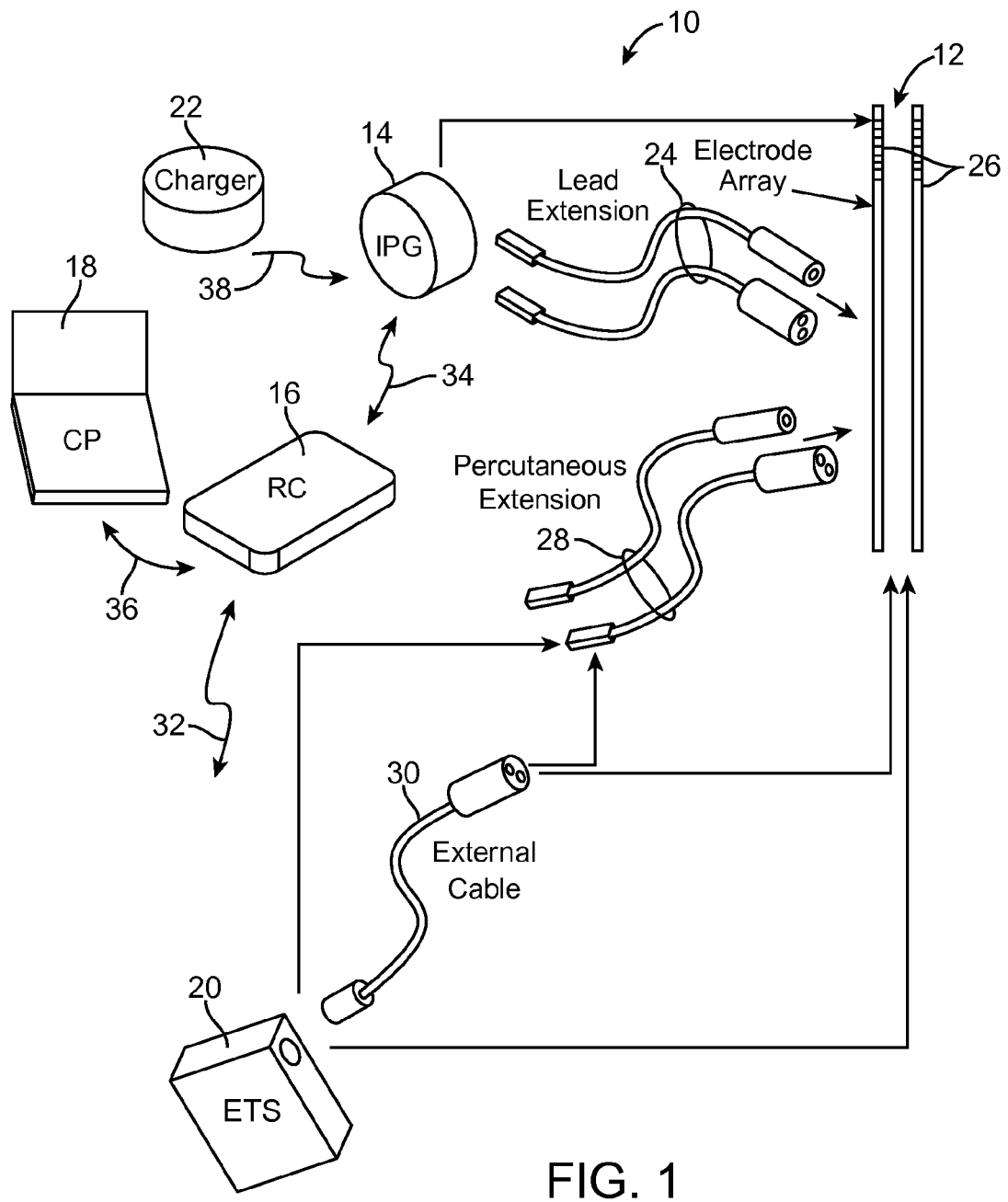
FIG. 1 is a plan view of a Spinal cord Stimulation (SCS) system constructed in accordance with one embodiment of the present inventions.

Turning first to FIG. 1, an exemplary SCS system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
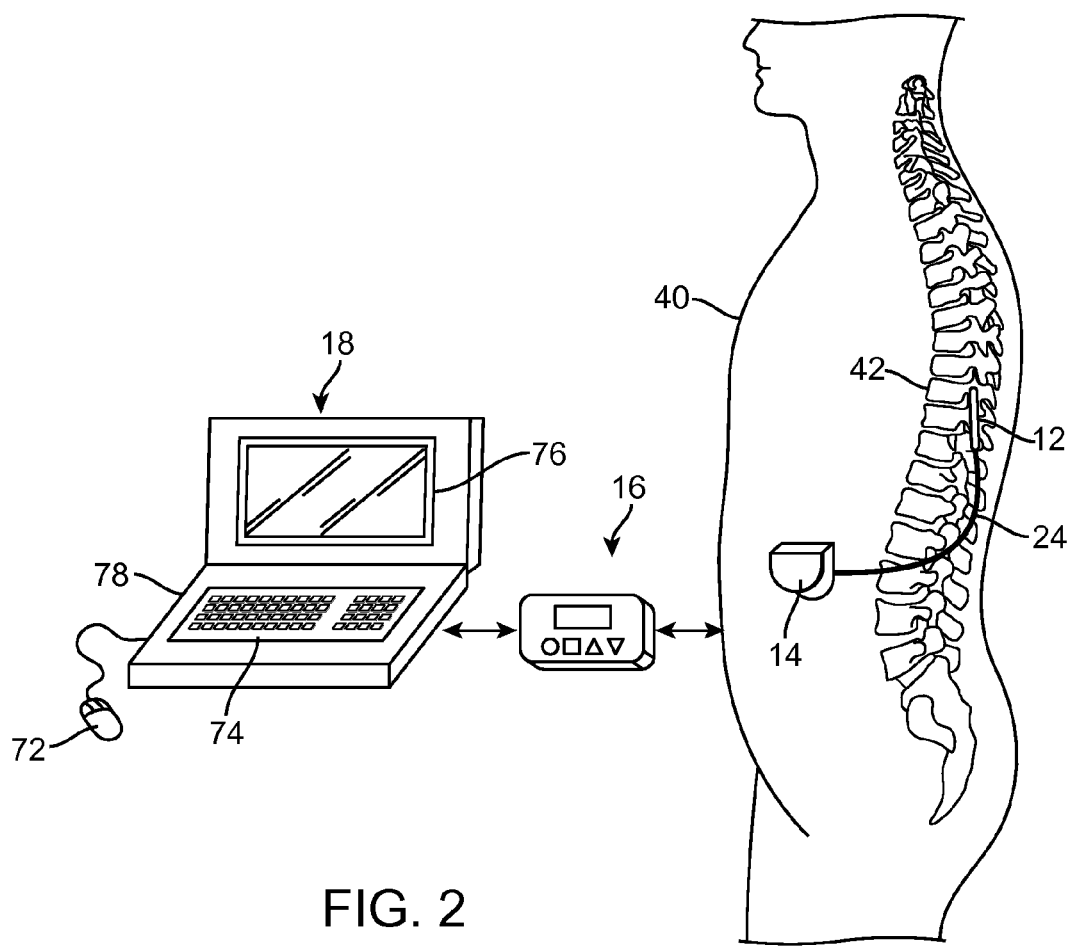
FIG. 2 is a perspective view of the arrangement of the SCS system of FIG. 1 with respect to a patient.

As shown in FIG. 2, the electrode leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
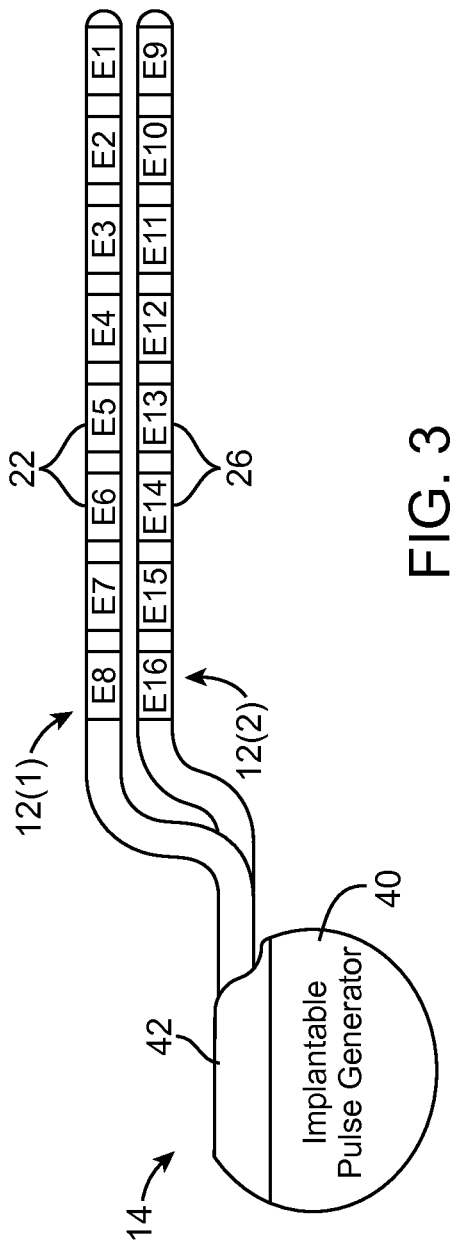
FIG. 3 is a profile view of an implantable pulse generator (IPG) and percutaneous leads used in the SCS system of FIG. 1.

Referring now to FIG. 3, the external features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the neurostimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode combinations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
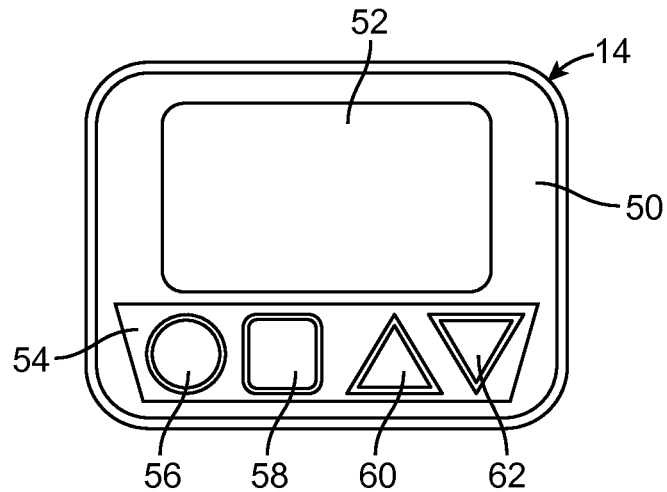
FIG. 4 is front view of a remote control (RC) used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
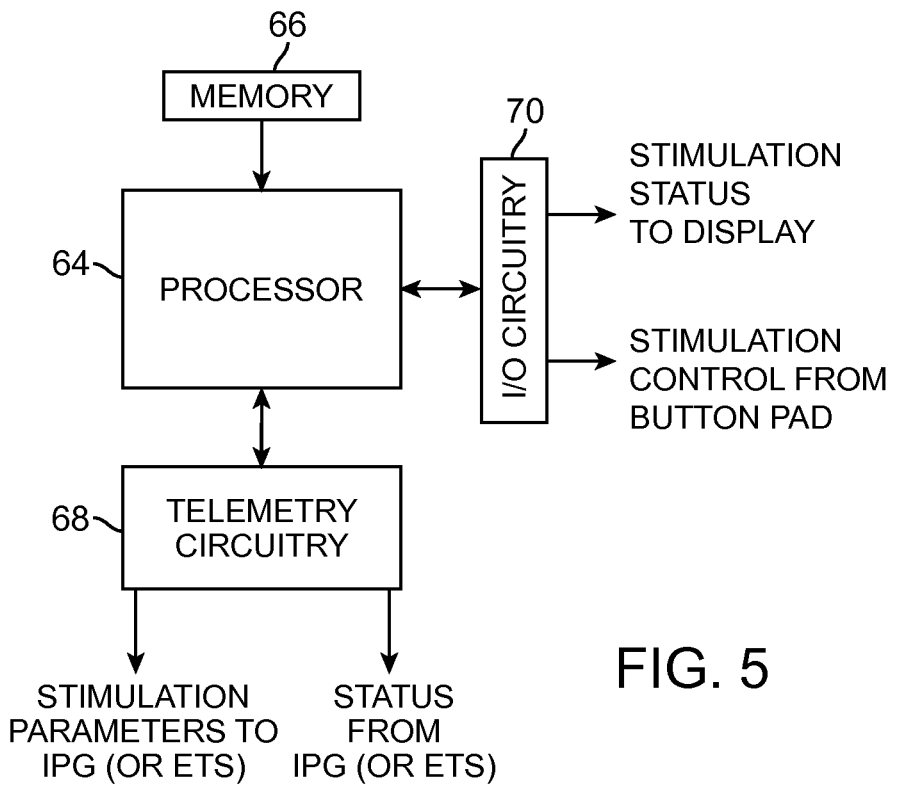
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
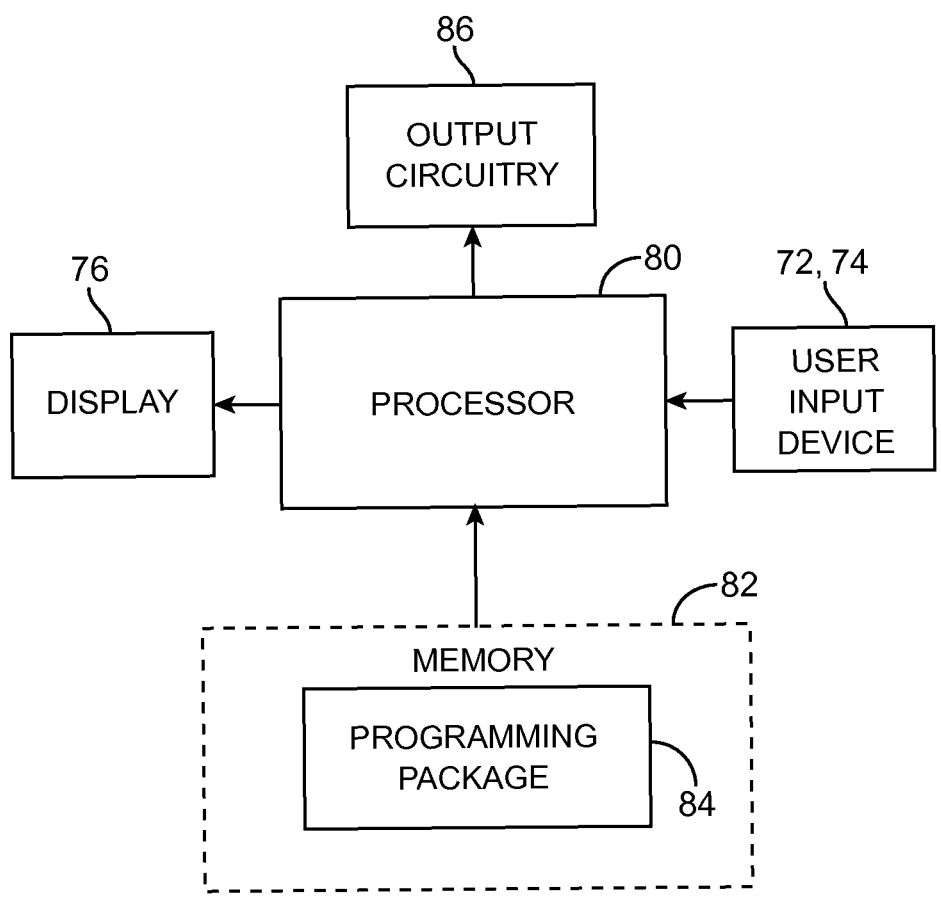
FIG. 6 is a block diagram of the internal components of a clinician's programmer (CP) used in the SCS system of FIG. 1.

Referring further to FIG. 6, to allow the user to perform these functions, the CP 18 includes a mouse 72, a keyboard 74, and a display monitor 76 housed in a housing 78. It is to be understood that in addition to, or in lieu of, the mouse 72, other directional programming devices may be used, such as a joystick, a button pad, a group of keyboard arrow keys, a roller ball tracking device, and horizontal and vertical rocker-type arm switches. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 further includes a processor 80 (e.g., a central processor unit (CPU)) and memory 82 that stores a stimulation programming package 84, which can be executed by the processor 80 to allow the user to program the IPG 14, and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side effects, along with metrics of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a more intuitive user interface that automatically manages the stimulation amplitude of the electrical stimulation energy as electrode configurations are manually or automatically transitioned.

Figure 7:
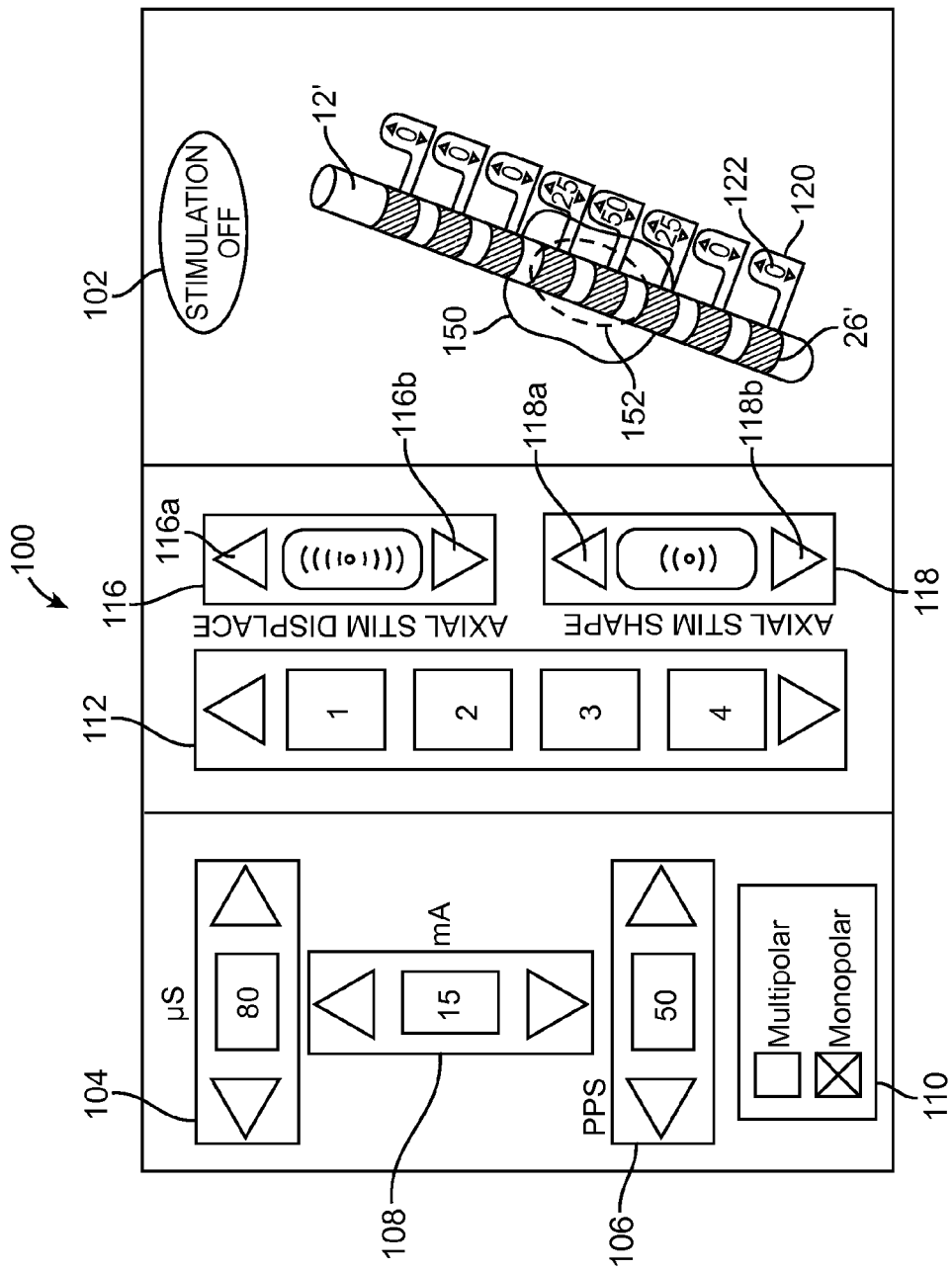
FIG. 7 is a plan view of a user interface of the CP of FIG. 6 for programming the IPG of FIG. 3.

In particular, a programming screen 100 can be generated by the CP 16, as shown in FIG. 7. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (μs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements.

The programming screen 100 also includes a set of axial electrical stimulation field displacement control elements 116 and a set of axial electrical stimulation field shaping control elements 118. In the illustrated embodiments, the control elements 116, 118, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial electrical stimulation field displacement control elements 116 is actuated, control signals are generated in response to which the processor 80 is configured for generating stimulation parameter sets designed to axially displace the locus of the electrical stimulation field relative to the axis of the lead 12. Preferably, the control signals that are generated in response to the actuation of the control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace the locus of the electrical stimulation field (i.e., along the axis of the lead 12) in the proximal direction; a lower arrow control element 116b can be clicked to axially displace the locus of the electrical stimulation field (i.e., along the axis of the lead 12) in the distal direction; a lower arrow control element 118a can be clicked to axially contract the electrical stimulation field about its locus, and an upper arrow control element 118b can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

The locus of the electrical stimulation field may alternatively be displaced using multiple timing channels. In particular, the electrical energy can be conveyed between different combinations of electrodes in accordance with multiple timing channels; that is, a first stimulating electrode group can be used during a first timing channel, a second stimulating electrode group can be used during a second timing channel, and so forth, and the groups may or may not overlap. The magnitude of the electrical energy conveyed in accordance with at least one of the multiple timing channels can be modified to effectively displace the locus of the stimulation region as experienced by the patient.

The electrical stimulation field can be expanded and contracted by gradually "steering" or shifting electrical current between electrodes in a similar manner described above with respect to the displacement of the locus of the electrical stimulation field, with the exception that the electrical stimulation field is expanded or contracted.

For example, the electrical stimulation field can be gradually expanded axially along the lead 12 by gradually including electrodes in a stimulating electrode group, and can be gradually contracted axially along the lead 12 by gradually excluding electrodes in a stimulating electrode group. The electrical stimulation field can be alternatively expanded and contracted using multiple timing channels in a similar manner described above with respect to the displacement of the locus of the electrical stimulation field, with the exception that the electrical stimulation field is expanded or contracted. For example, the magnitude of the electrical energy conveyed in accordance with at least one of the multiple timing channels can be modified to effectively expand or contract the stimulation field.

Further details discussing different techniques for modifying an electrical stimulation field is disclosed in U.S. Provisional Patent Application 61/374,879, entitled "User Interface for Segmented Neurostimulation Leads," which is expressly incorporated herein by reference. In an optional embodiment, additional control elements can be provided to circumferentially displace the locus of the electrical stimulation field, circumferentially contract or expand the electrical stimulation field, radially displace the locus of the electrical field, or radially contract or expand the electrical stimulation field, as disclosed in U.S. Provisional Patent Application 61/374,879.

Although the programming screen 100 illustrates only one neurostimulation lead 12 with electrodes arranged in only one dimension, thereby allowing the electrical current to only be steered in one dimension, it should be appreciated that the programming screen 100 may additionally illustrate the other neurostimulation lead 12, thereby arranging the electrodes in two dimensions and allowing the electrical current to be steered in two dimensions. In this case, using appropriate control elements (e.g., left and right arrows), the locus of the electrical stimulation field can be displaced in the transverse direction (perpendicular to the axial direction, and in this case, left or right) and/or the electrical stimulation field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

The programming screen 100 displays three-dimensional graphical renderings of the lead 12' and electrodes 26'. In an optional embodiment, iconic control elements 120 are graphically linked to the three-dimensional electrode renderings 26'. Continual actuation of the control elements 120 generates control signals that prompt the processor 80 to generate stimulation parameters designed to modify the electrical stimulation field, which stimulation parameters are then transmitted from the output circuitry 86 of the CP 18 to the IPG 14. In the illustrated embodiment, each of the control elements 120 has an up arrow and a down arrow that can be respectively actuated (e.g., by clicking) to respectively increase or decrease the electrical current flowing through the electrode 26 corresponding to the graphical electrode rendering 26' to which the actuated control element 120 is graphically linked.

Actuation of any of the control elements 120 essentially steers electrical current from other active electrodes to the electrode associated with the actuated control element 120 or from the electrode associated with the actuated control element 120 to other active electrodes. In this manner, the locus of the electrical stimulation field can be displaced, the shape of the electrical stimulation field can be modified, and if two separate electrical stimulation fields current exist, electrical current can be shifted from one of the electrical stimulation fields (effectively decreasing its size) to another of the electrical stimulation fields (effectively increasing its size).

The control element 120 also includes an indicator 122 that provides an indication of the amount of electrical current flowing through each of the electrodes 26 in terms of a fractionalized current value. The indicators 122 may perform this function when the respective control elements 120 are actuated or when the axial electrical stimulation field displacement control elements 116 and axial electrical stimulation field shaping control elements 118 are actuated. The programming screen 100 displays the three-dimensional graphical renderings of the lead 12' and electrodes 26' relative to a graphical representation of the anatomical structure 150 that is preferably the stimulation target. The processor 80 computes an estimate of a resulting volume of activation (VOA) 152, and generates display signals that prompt the monitor 76 to display a graphical representation of the VOA 152 with the graphical lead 12' and graphical anatomical structure 150. In the preferred embodiment, the graphical VOA 152 is superimposed over the graphical anatomical structure 150. Further details discussing technique for computing the estimate of a VOA are disclosed in A. M. M. Frankemolle, et al., *Reversing Cognitive-Motor Impairments in Parkinson's Disease Patients Using a Computational Modelling Approach to Deep*

*Brain Stimulation Programming*, Brain 2010; pp. 1-16), which is expressly incorporated herein by reference.

As briefly discussed above, the user interface manages the amplitude of the electrical stimulation energy between transitions between electrode configurations, and in this case, fractionalized electrode configurations. The management amplitude technique described herein estimates the stimulation amplitude based on the electric field theoretically generated from an electrode configuration. Notably, in extracellular neural stimulations, the generated electric field drives the activation of neuronal elements, and the threshold amplitude required to stimulate one or more of the neuronal elements depends on the electric field distribution and the properties of the neuronal elements. The amplitude estimate will be based on proper modeling of the electric field as well as the neuronal elements. The amplitude management technique described herein can be applied step-by-step for a continuation change of electrode configuration. This will allow for an automated step-by-step adjustment of stimulation amplitude in order to maintain the stimulation strength. Although the automated adjustment of the amplitude may not completely eliminate the need for manual amplitude adjustment based on patient needs, the amplitude management technique provides a generalized approach to manage the amplitude changing during programming when different electrode configurations are navigated.

Figure 8:
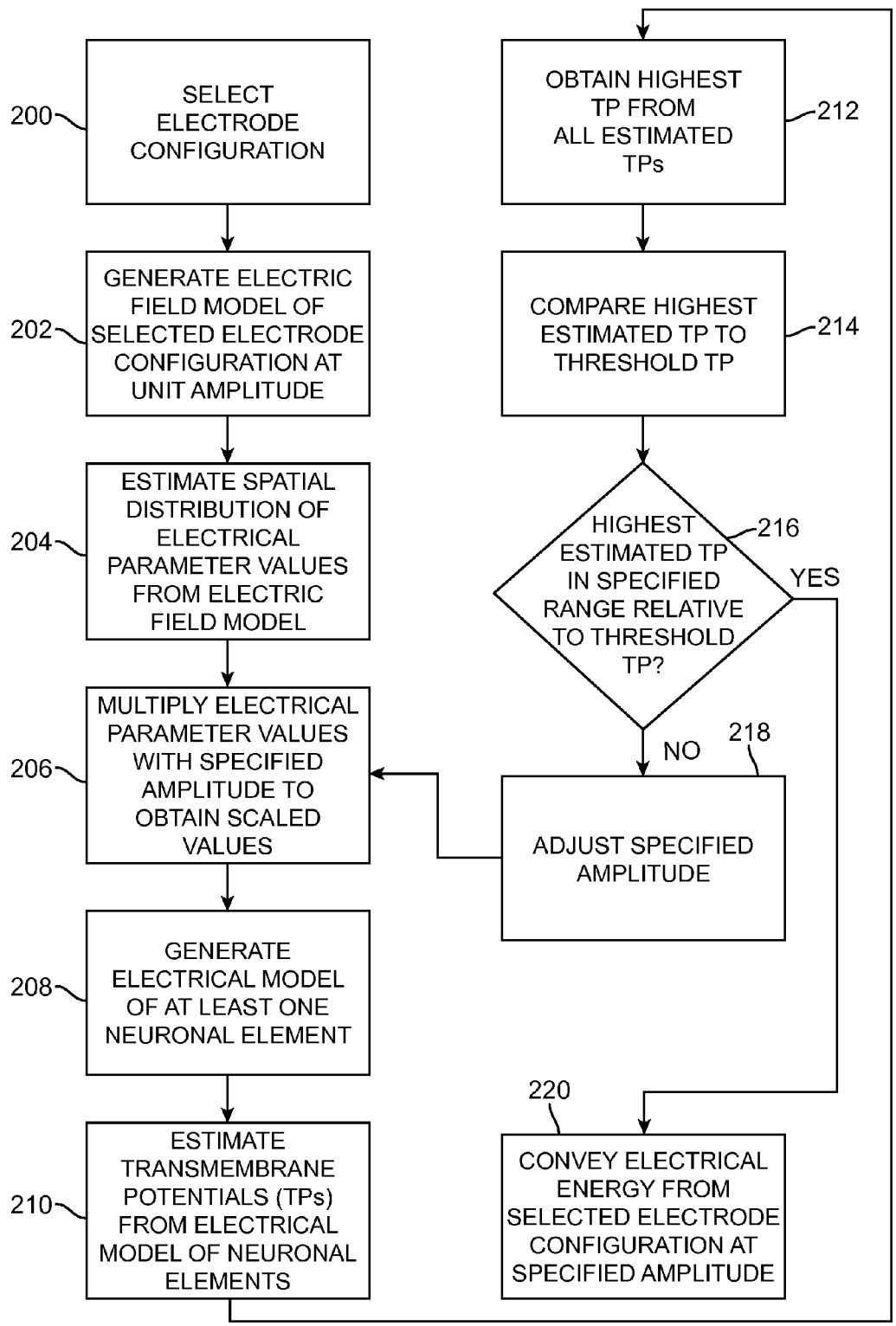
FIG. 8 is a flow diagram illustrating one method of managing the amplitude of electrical energy between electrode configuration transitions.

In particular, and with reference to FIG. 8, the processor 80 selects an electrode configuration (which may be an arbitrary electrode configuration or may be selected from a predefined plurality of electrode configurations) in response to receiving input from the user via the programming screen 100, as described above (step 200). Next, the processor 80 predicts a neural response in the patient induced by electrical energy theoretically conveyed by the selected electrode configuration (steps 202-210). The electrical energy has a specified theoretical amplitude. In the illustrated embodiment, since current sources are used to actually generate the electrical energy, the specified theoretical amplitude may conveniently be a specified amperage value. Alternatively, if voltage sources are used to actually generate the electrical energy, the specified theoretical amplitude may conveniently be a specified voltage value.

As one example, the processor 80 predicts the neural response by first generating an electrical field model of the selected electrode configuration at a reference amplitude (e.g., a unit amplitude) in a conventional manner (step 202). The electric field model may be, e.g., a three-dimensional analytical model or a numerical model (e.g., a finite element model (FEM) or a boundary element model (BEM)). Each electrode may be modeled with one or more point sources, as described in U.S. patent application Ser. No. 12/904,933, entitled "System and Method for Modeling Electrode Morphologies," which is expressly incorporated herein by reference. The electric field model can take into account the tissue medium in which the neurostimulation lead is implanted, which may be assumed to have a uniform conductivity of 0.3 S/m and comprise a sheath of encapsulation tissue surrounding the neurostimulation lead having a thickness of 0.2 mm and a conductivity of 0.15 S/m. Alternatively, the electric field model can take in account a tissue medium of non-uniformity conductivity, as described in U.S. Pat. No. 7,627,384, which is expressly incorporated herein by reference.

After generating the electrical field model, the processor 80 may solve the model to estimate a spatial distribution of electrical parameter values induced by electrical energy theoretically conveyed from the electrode configuration (step 204). In the preferred embodiment, each of the electrical parameter values is in a linear relationship with the amplitude of the electrical energy conveyed from the electrode configuration. For example, in the illustrated embodiment, the electrical parameter values are field potential values, although other types of electrical parameters, such as electrical field values, current density values, etc., can be used.

Next, the processor 80 multiplies the estimated spatial distribution of electrical parameter values with the specified amplitude of the electrical energy theoretically conveyed from the electrode configuration to obtain a spatial distribution of scaled electrical parameter values (step 206).

Next, the processor 80 generates an electrical model of at least one neuronal element in the patient in a conventional manner (step 208), and estimates the neural response of the neuronal element(s) based on the electrical neuronal model (step 210). In the illustrated embodiment, the neural response is a transmembrane potential, although other parameters, such as transmembrane conductivity or transmembrane current, which can be derived as a function of the transmembrane potential, can be used. In the illustrated embodiment, a multitude of axially aligned neuronal elements are modeled around the electrode configuration, and the transmembrane potentials at the Nodes of Ranvier of each of the neuronal elements are estimated. The neuronal elements are preferably modeled with appropriately selected properties (e.g., morphological and electrical properties), and the time course and distribution of the induced transmembrane potential is calculated over the neuronal elements. The electrical neuron model may be, e.g., a passive neuron model, an active neuron model, or an analog chip based circuit model. The induced transmembrane potential may be estimated, e.g., using one of an activating function (i.e., the $2^{nd}$ spatial derivative of the extracellular electric field along the axis of each neuronal element) or a driving function (i.e., a weighted average of the activating function at a node of Ranvier and those at the adjacent nodes along the neuronal element), or a $1^{st}$ spatial derivative of the extracellular electric field along the axis of each neuronal element.

Further details discussing the modeling of neuronal elements in response to an induced electric field are described in U.S. Pat. No. 7,627,384, Eduardo N. Warman, *Modeling the Effects of Electric Fields on Nerve Fibers: Determination of Excitation Thresholds*, IEEE Transactions on Biomedical Engineering, Vol. 39, No. 12, December 1992, and U.S. Patent Application Ser. No. 61/427,059, which is expressly incorporated herein by reference.

After the processor 80 predicts the neural response induced by electrical energy theoretically conveyed by the selected electrode configuration at steps 202-210, the processor 80 derives a metric value from the predicted neural response, and in particular, from the estimated transmembrane potentials (step 212), and compares this metric value to a reference threshold value (step 214). In the embodiment illustrated in FIG. 8, the derived metric value is the highest transmembrane potential of all of the Nodes of Ranvier, and the reference threshold value is the threshold transmembrane potential at which an action potential is evoked within a neuron of the patient.

Because the threshold transmembrane potential may vary between patients and may vary between regions in the patient (e.g., the threshold transmembrane potential may differ within the neurons of the spinal cord and the neurons of the brain), the threshold transmembrane potential for a specific stimulation region of a patient may not be initially known. The threshold transmembrane potential of the patient may be determined empirically. For example, the processor 80 may instruct the IPG 14 to deliver reference electrical energy at a known amplitude to a reference electrode configuration, adjusting the known amplitude of the reference electrical energy until a perception threshold of the patient is met or exceeded (which may be based on verbal feedback from the patient), and estimating a transmembrane potential of at least one reference neuron of the patient that would be induced by the reference electrical energy of the reference threshold amplitude by the reference electrode configuration (e.g., by performing steps 202-210 of FIG. 8 using the known amplitude and reference electrode configuration). The estimated transmembrane potential can thus be used as the threshold transmembrane potential for all subsequently tested electrode configurations. Once the threshold transmembrane potential is obtained, it can be used to calibrate or derive threshold transmembrane potentials for other reference electrical energy (for example, pulses of various PW), if such a calibration curve is known. In another embodiment, the threshold transmembrane potentials for various reference electrical energy (e.g., as a function of PW) can be determined offline and then stored in the memory.

If the highest estimated transmembrane potential is not in a specified range relative to the threshold transmembrane potential (step 216), the processor 80 automatically adjusts the specified amplitude of the electrical energy theoretically conveyed by the electrode configuration (step 218), and then repeats steps 202-216 using the adjusted theoretical amplitude as the specified theoretical amplitude. In one embodiment, the theoretical amplitude is adjusted in uniform increments. For example, if the specified theoretical amplitude is amperage, it can be adjusted in increments of 0.1 mA.

In one example, if the highest estimated transmembrane potential is below the threshold transmembrane potential, so that the electrical energy, if actually conveyed by the electrode configuration, would not stimulate tissue within the patient, the processor 80 may automatically increase the specified theoretical amplitude, so that the next highest estimated transmembrane potential will be closer to the threshold transmembrane potential. Once the highest estimated transmembrane potential meets or exceeds the threshold transmembrane potential, the processor 80 will stop increasing the specified theoretical amplitude.

In another example, if the highest estimated transmembrane potential is above the threshold transmembrane potential by a specified difference value (e.g., greater than 10 mV above threshold transmembrane potential), so that the electrical energy, if actually conveyed by the electrode configuration, may cause undesirable side effects to the patient, the processor 80 may automatically decrease the specified theoretical amplitude, so that the next highest estimated transmembrane potential will be closer to the threshold transmembrane potential. Once the highest estimated transmembrane potential is within the specified difference value of the threshold transmembrane potential, the processor 80 will stop decreasing the specified theoretical amplitude.

If the highest estimated transmembrane potential is within the specified range relative to the threshold transmembrane potential (step 216), the processor 80 instructs the IPG 14 via the telemetry circuitry 86 to deliver the electrical energy at the specified theoretical amplitude via the selected electrode configuration to stimulate the neuronal element(s) (step 220). The processor 80 may then select another electrode configuration in response to receiving input from the user via the programming screen 100, and determine the desired amplitude of the electrical energy to be conveyed from the other electrode configuration in accordance with steps 202-220.

Although the technique illustrated in FIG. 8 considers the neural response of an individual neuronal element in determining the adjustment of the specified amplitude, the response of a population of neuronal elements may be evaluated, in which case, a metric value different from the highest estimated transmembrane potential, and in particular a volume of activation (VOA), may be analyzed to determine the desired amplitude for the electrical energy.

Figure 9:
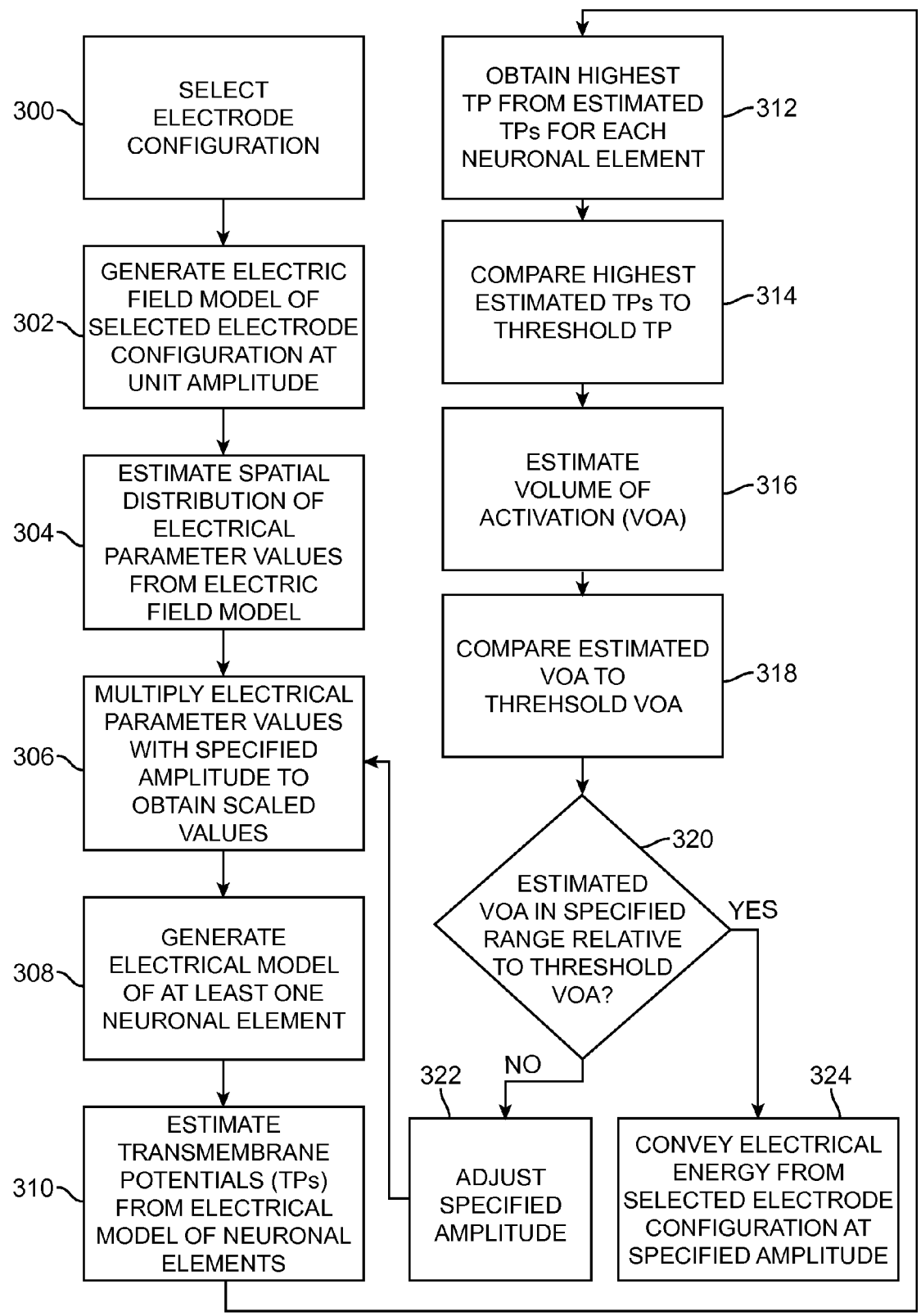
FIG. 9 is a flow diagram illustrating another method of managing the amplitude of electrical energy between electrode configuration transitions.

In particular, and with reference to FIG. 9, the processor 80 selects an electrode configuration in response to receiving input from the user via the programming screen 100, and predicts a neural response in the patient induced by electrical energy theoretically conveyed by the selected electrode configuration in the same manner discussed above with respect to FIG. 8 (steps 302-310). However, instead of using the highest transmembrane potential of all of the Nodes of Ranvier as the metric value, and a threshold transmembrane potential as the reference threshold value, a volume of activation is used as the metric value, and a threshold volume of activation is used as the reference threshold value.

In particular, the processor 80 obtains the highest transmembrane potential along the Nodes of Ranvier for each neuronal element (step 312), compares them to the threshold transmembrane potential (step 314), and determines based on these comparisons, the neuronal elements that are activated, and thus, the estimated volume of activation (step 316). The processor 80 then compares the estimated volume of activation with the threshold volume of activation (step 318). If the estimated volume of activation is not in a specified range relative to the threshold volume of activation (step 320), the processor 80 automatically adjusts the specified amplitude of the electrical energy theoretically conveyed by the electrode configuration (step 322), and then repeats steps 302-322 using the adjusted theoretical amplitude as the specified theoretical amplitude.

In one example, if the estimated volume of activation is below the threshold volume of activation by a specified difference value, so that the electrical energy, if actually conveyed by the electrode configuration, may not stimulate enough of the targeted tissue, the processor 80 may automatically increase the specified theoretical amplitude, so that the next estimated volume of activation will be closer to the threshold volume of activation. Once the estimated volume of activation is within the specified difference value of the threshold volume of activation, the processor 80 will stop increasing the specified theoretical amplitude.

In another example, if the estimated volume of activation is above the threshold volume of activation by a specified difference value, so that the electrical energy, if actually conveyed by the electrode configuration, may stimulate non-targeted tissue, the processor 80 may automatically decrease the specified theoretical amplitude, so that the next estimated volume of activation will be closer to the threshold volume of activation. Once the estimated volume of activation is within the specified difference value of the threshold volume of activation, the processor 80 will stop decreasing the specified theoretical amplitude.

If the estimated volume of activation is within the specified range relative to the threshold volume of activation (step 318), the processor 80 instructs the IPG 14 via the telemetry circuitry 86 to deliver the electrical energy at the specified theoretical amplitude via the selected electrode configuration to stimulate the targeted tissue (step 324). The processor 80 may then select another electrode configuration in response to receiving input from the user via the programming screen 100, and determine the desired amplitude of the electrical energy to be conveyed from the other electrode configuration in accordance with steps 302-324.

In another amplitude management technique, the amplitude of a currently selected electrode configuration is adjusted relative to a known amplitude of a previously selected electrode configuration using scaling factors computed from the estimated theoretical amplitudes (or alternatively, the metric value) for the selected electrode configurations determined in accordance with the techniques illustrated in FIGS. 8 and 9. If the estimated transmembrane potentials for different electrode configurations are computed in a consistent manner and compared to the same threshold transmembrane potential, the relative changes in the scaling factors can be used to estimate the relative adjustments (boosting value) in amplitude that are required to maintain the stimulation strength during electrode configuration transitions, assuming the threshold transmembrane potential is relatively invariant for the patient. As such, only the relative values of the estimated transmembrane potentials between the different electrode configurations are of concern, and the reference threshold value to which the metric values are compared need not be accurate as long as a reasonable value is selected for the reference threshold value and the same reference threshold value is used for the selected electrode configurations.

Figure 10:
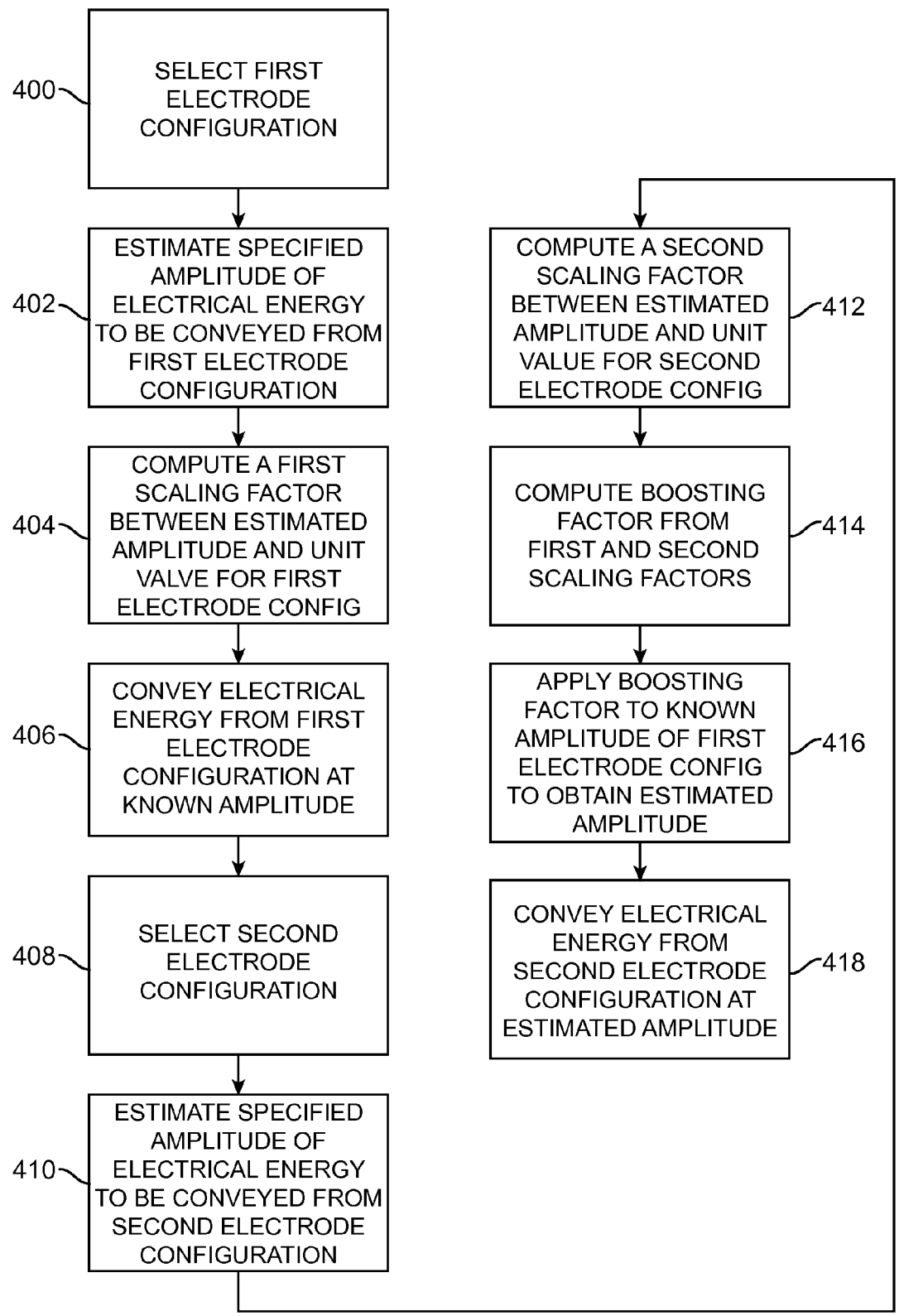
FIG. 10 is a flow diagram illustrating still another method of managing the amplitude of electrical energy between electrode configuration transitions.

In particular, and with reference to FIG. 10, the processor 80 selects a first electrode configuration in response to receiving input from the user via the programming screen 100 in the same manner described above with respect to step 200 of FIG. 8 or step 300 of FIG. 9 (step 400), and estimates the specified amplitude of the electrical energy to be conveyed from the first electrode configuration in the same manner described above with respect to steps 202-218 of FIG. 8 or steps 302-322 of FIG. 9 (step 402). The processor 80 then computes a first scaling factor between the estimated specified amplitude (or alternatively, the metric value) and a unit amplitude for the first electrode configuration (step 404). For example, since the spatial distribution of field potentials are computed from a unit amplitude of the electrical energy, the scaling factor is proportional to the predicted amplitude of the electrical energy, and thus, the scaling factor may be the number used in the last iteration to multiply the unit value spatial distribution of field potentials at step 206 of FIG. 8 or step 306 of FIG. 9.

The processor 80 then directs the IPG 14 to actually convey the electrical energy from the first electrode configuration at the estimated amplitude (step 406), and then determines an amplitude of the electrical energy known to stimulate the targeted tissue of the patient without causing side effects (step 408). This known amplitude can be the amplitude predicted at step 404 if it is discovered that the electrical energy with this amplitude does, in fact, stimulate the targeted tissue of the patient without causing side effects, or may be amplitude different from the predicted amplitude (e.g., if the electrical energy at the predicted amplitude does not stimulate tissue or creates side effects, the user, based on feedback from the patient, may manually adjust the amplitude of the electrical energy until the targeted tissue is stimulated without side effects).

The processor 80 selects a second electrode configuration in response to receiving input from the user via the programming screen 100 in the same manner described above with respect to step 200 of FIG. 8 or step 300 of FIG. 9 (step 410), and estimates the specified amplitude of the electrical energy to be conveyed from the second electrode configuration in the same manner described above with respect to steps 202-218 of FIG. 8 or steps 302-322 of FIG. 9 (step 412). The processor 80 then computes a second scaling factor between the estimated amplitude (or alternatively, the metric value) and a unit amplitude for the second electrode configuration (step 414).

The processor 80 then computes a boosting factor based on the first and second scaling factors (step 416), applies the boosting factor to the known amplitude of the electrical energy conveyed by the first electrode configuration to generate the estimated amplitude for the second electrode configuration (step 418), and instructs the IPG 14 to actually convey the electrical energy from the second electrode configuration at the predicted amplitude (step 406). In the illustrated embodiment, the boosting factor is computed in accordance with the equation $BF=(SF_B-SF_A)/SF_A$, wherein BF is the boosting factor, $SF_A$ is the first scaling factor, and $SF_B$ is the second scaling factor, and the boosting factor is applied to the known amplitude in accordance with the equation $A_{EST}=A_{KNOWN}\times(1+BV)$, where $A_{EST}$ is the estimated amplitude, and $A_{KNOWN}$ is the known amplitude.

Although the foregoing techniques have been described as being implemented in the CP 18, it should be noted that this technique may be alternatively or additionally implemented in the RC 16, and the processing functions of the technique can even be performed in the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
   (a) receiving input from a user;
   (b) selecting a first electrode configuration in response to receiving the input from the user via the user input device;
   (c) predicting a neural response in the patient induced by electrical energy theoretically conveyed by the first electrode configuration at a specified amplitude;
   (d) deriving a metric value from the predicted neural response;
   (e) comparing the metric value to a reference threshold value;
   (f) adjusting the specified amplitude of the electrical energy if the metric value is not in a specified range relative to the reference threshold value;
   (g) repeating steps (c)-(f) using the adjusted amplitude as the specified amplitude until the metric value is in the specific range relative to the reference threshold value; and
   (h) instructing a neurostimulation device to deliver the electrical energy at the adjusted amplitude via the first electrode configuration to stimulate the patient.

2. The method of claim 1, wherein the first electrode configuration is a fractionalized electrode configuration.

3. The method of claim 1, wherein the specified amplitude of the electrical energy theoretically conveyed by the first electrode configuration is adjusted in uniform increments.

4. The method claim 1, wherein the specified amplitude of the electrical energy theoretically conveyed by the first electrode configuration is increased if the metric value is below the reference threshold value.

5. The method of claim 1, wherein the specified amplitude of the electrical energy theoretically conveyed by the first electrode configuration is decreased if the metric value exceeds the reference threshold value by more than a specific difference value.

6. The method of claim 1, wherein the metric value is an estimated transmembrane potential of at least one neuronal element, and the reference threshold value is a threshold transmembrane potential.

7. The method of claim 1, wherein the metric value is an estimated volume of activation, and the reference threshold value is a threshold volume of activation.

8. The method of claim 1, wherein the neural response in the patient is predicted by estimating a spatial distribution of electrical parameter values induced by electrical energy theoretically conveyed by the first electrode configuration at a unit amplitude value, multiplying the electrical parameters by the specified amplitude to obtain a spatial distribution of scaled electrical parameter values, and estimating a transmembrane potential of at least one neuronal element in the patient in response to the scaled electrical parameters.

9. The method of claim 8, wherein the electrical parameter values are in a linear relationship with the specified amplitude of the electrical energy theoretically conveyed by the first electrode configuration.

10. The method of claim 8, wherein each of the electrical parameter values is selected from one of a field potential value, an electrical field value, and a current density value.

11. The method of claim 8, wherein the neural response in the patient is predicted by generating an electric field model of the first electrode configuration, and generating an electrical model of the at least one neuronal element, wherein the electrical parameter values are estimated based on the electric field model of the first electrode configuration, wherein the transmembrane potential is estimated based on the electrical model of the at least one neuronal element.

12. The method of claim 11, wherein the electric field model is one of an analytical model and a numerical model, and the electrical model of the at least one neuronal element is one of a passive neuron model, an active neuron model, and an analog chip based circuit model.

13. The method of claim 11, wherein the induced transmembrane potential is estimated using one of an activating function and a total driving function of the electrical model of the at least one neuronal element.

14. The method of claim 1, wherein the amplitude of the electrical energy theoretically conveyed by the first electrode configuration is an amperage value.

15. The method of claim 1, wherein the amplitude of the electrical energy theoretically conveyed by the first electrode configuration is a voltage value.

16. The method of claim 1, wherein the neurostimulation device is instructed to deliver reference electrical energy at a known amplitude to a reference electrode configuration, the reference amplitude of the reference electrical energy is adjusted until a perception threshold of the patient is met or exceeded, a transmembrane potential of at least one reference neuron of the patient is that would be induced by the reference electrical energy of the reference amplitude by the reference electrode configuration is estimated, and the reference threshold value is derived based on the estimated transmembrane potential of the at least one reference neuron.

17. The neurostimulation system of claim 1, further comprising:
(i) selecting a second different electrode configuration in response to receiving the input from the user; and
(j) repeating steps (c)-(h) for the second electrode configuration.

18. The method of claim 17, wherein the user input comprises directional signals.

19. The method of claim 1, further comprising:
(i) determining a first scaling factor for the first electrode configuration;
(j) instructing the neurostimulation device to deliver the electrical energy at a known amplitude via the first electrode configuration to stimulate the patient;
(k) selecting another different electrode configuration in response to receiving the input from the user;
(l) repeating steps (c)-(g) for the second electrode configuration;
(m) determining a second scaling factor for the second electrode configuration;
(n) computing a boosting factor based on the first and second scaling factors;
(o) applying the boosting factor to the known amplitude to generate an estimated amplitude; and
(p) instructing the neurostimulation device to deliver the electrical energy at the estimated amplitude via the second electrode configuration to stimulate the patient.

20. The method of claim 19, wherein the first scaling factor is between the adjusted amplitude for the first electrode configuration and a reference amplitude, and the second scaling factor is between the adjusted amplitude for the second electrode configuration and the reference amplitude.

21. The method of claim 19, wherein the first scaling factor is between the metric value for the first electrode configuration and a reference metric value at a reference amplitude, and the second scaling factor is between the metric value for the second electrode configuration and the reference metric value at the reference amplitude.

22. The method of claim 19, wherein the known amplitude is the adjusted amplitude.

23. The method of claim 19, wherein the known amplitude is different from the adjusted amplitude.

24. The method of claim 19, wherein the boosting factor is computed in accordance with the equation $BF=(SF_B-SF_A)/SF_A$, wherein BF is the boosting factor, $SF_A$ is the first scaling factor, and $SF_B$ is the second scaling factor.

25. The method of claim 19, wherein the boosting factor is applied to the known amplitude in accordance with the equation $A_{EST}=A_{KNOWN}\times(1+BV)$, where $A_{EST}$ is the estimated amplitude, and $A_{KNOWN}$ is the known amplitude.

26. The method of claim 1, wherein the patient is suffering from chronic pain, and the therapy comprises alleviation of the chronic pain.

* * * * *